US006204004B1

(12) United States Patent
Kaper et al.

(10) Patent No.: US 6,204,004 B1
(45) Date of Patent: Mar. 20, 2001

(54) **IMMUNODIAGNOSTIC TEST FOR ENTEROHEMORRHAGIC *ESCHERICHIA COLI* INFECTION**

(75) Inventors: James B. Kaper, Pasadena; Karen Jarvis, Arnold, both of MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 08/821,872

(22) Filed: Mar. 21, 1997

(51) Int. Cl.$^7$ .................................................. G01N 33/569
(52) U.S. Cl. ......................... 435/7.37; 435/7.32; 435/6; 536/23.1; 530/402
(58) Field of Search ............................... 536/23.1; 435/6, 435/7.37; 426/87; 530/402

(56) References Cited

U.S. PATENT DOCUMENTS

| | | | |
|---|---|---|---|
| 5,451,504 | * 9/1995 | Fitzpatrick et al. | 435/7.2 |
| 5,552,294 | * 9/1996 | Thorne | 435/7.32 |
| 5,747,272 | * 5/1998 | O'Brien et al. | 435/7.37 |
| 5,747,293 | * 5/1998 | Dougan et al. | 530/402 |
| 5,753,285 | * 5/1998 | Horan | 426/87 |
| 5,756,293 | * 5/1998 | Hall et al. | 435/6 |
| 5,798,260 | * 8/1998 | Tarr et al. | 435/252.3 |

FOREIGN PATENT DOCUMENTS

97/00265   10/1997  (WO).

OTHER PUBLICATIONS

Chart, H et al, Journal of Clinical Microbiology, Feb. 1989, vol. 27(2), pp. 285–290, 1989.*
Chart and Griffiths, "Antigenic and Molecular Homology of the Ferric Enterobactin Receptor Protein of *Escherichia coli*," *Journal of General Microbiology* 131:1503–9 (1985).
Filip, Fletcher, Wulff, Earhart, "Solubilization of the Cytoplasmic Membrane of *Escherichia coli* by the Ionic Detergent Sodium–Lauryl Sarcosinate," *Journal of Bacteriology* 115/3:717–22 (1973).
Chart and Trust, "Acquisition of Iron by *Aeromonas salmonicida*," *Journal of Bacteriology* 156/2:758–64 (1983).
Osborn, Gander, Parisi, Carson, "Mechanism of Assembly of the Outer Membrane of *Salmonella typhimurium*," *Journal of Biological Chemistry* 247/12:3962–72 (1972).
Kenney, B et al (1995), Aug. 15, Proc. Nat'l Acad. Sci, vol. 92, p. 7991–7995.*
Haigh, R. et al (1995), FEMS Microbiol. Letters, vol. 129 (1), p. 63–68.*
Debray C. et al (1995), Infect. Immun., Aug., vol. 63(8), p. 2873–2879.*
Frankel, D. et al (1996), Infect. Immun., vol. 64(12), p. 5315–5325.*
Gomez, O. (1993), Diss. Abs. Int., vol. 55 (06–B) p. 2077.*
Gomez Duarte et al (1995), Infect. Immun., May, vol. 63(5), p. 1767–1776.*
Jerse, A. E. et al (1991), Infect. Immun., Dec. 1991, vol. 59(12), p. 4302–4309.*
McDaniel, T. K et al (1995) Proc–Nat'l Acad. Sci (USA) Feb., vol. 92, pp. 1664–1668.*
Agin, T. S. et al (1996), FEMS Microbiol. Let., vol. 144, pp. 249–258.*

(List continued on next page.)

*Primary Examiner*—Lynette R. F. Smith
*Assistant Examiner*—Ginny Allen Portner
(74) *Attorney, Agent, or Firm*—Chalin A. Smith; David L. Marks (57) ABSTRACT

Several EHEC proteins which are secreted into the culture supernatant have been discovered. These proteins are not produced by non-pathogenic *E. coli*, and produce a strong serum antibody response in patients with HUS and bloody diarrhea.

12 Claims, 7 Drawing Sheets

BOVINE ANTIBODY RESPONSES TO Esp B (2ug/ml) PURIFIED FROM E.coli 0157:H7 STRAIN 93–111. SERA FROM TWO CATTLE (835 AND M38) WERE WERE TESTED ON DAY 0 (UNINFECTED) AND 38 (835) OR 25 (M38) WEEKS AFTER INFECTION.

OTHER PUBLICATIONS

Donnenberg, M. S. (1993), Aug., J. Bacteriol, vol. 175 (15), p. 4670–4680.*
Jarvis, K. G. et al (Aug. 1995), Proc. Nat'l Acad Sci, vol. 92, p. 7996–8000.*
Willen, L. H. et al (1996), J. Clin. Microbiol, Dec., vol. 34(12), p. 2980–2984.*

Johnson, R. P. et al (1996), Infect. Immun., vol. 54(5), May, p. 1879–1883.*

Karmali, M. A. et al, (1994) Jun., J. Clin. Microbiol, vol. 32(6), p. 1457–1463.*

* cited by examiner

BOVINE ANTIBODY RESPONSES TO Esp B (2ug/ml) PURIFIED FROM E.coli O157:H7 STRAIN 93-111. SERA FROM TWO CATTLE (835 AND M38) WERE WERE TESTED ON DAY 0 (UNINFECTED) AND 38 (835) OR 25 (M38) WEEKS AFTER INFECTION.

HUMAN ANTIBODY RESPONSES TO Esp B (2ug/ml) PURIFIED FROM E.coli O157:H7 STRAIN 93-111. HS366 AND 274-0013 ARE FROM HUS PATIENTS INFECTED WITH O157:H7 E.coli. O24 IS A NEGATIVE CONTROL.

FIG.7

IMMUNODIAGNOSTIC TEST FOR ENTEROHEMORRHAGIC ESCHERICHIA COLI INFECTION

The development of the present invention was supported by the University of Maryland, Baltimore, Md. and by funding from the National Institutes of Health (Contract Number AI 21657). The United States Government has a non-exclusive, irrevocable, paid-up license to practice or have practiced for or on behalf of the United States the invention herein as provided for by the terms of the above mentioned contracts awarded by the United States Government.

FIELD OF THE INVENTION

The present invention relates to novel proteins which are secreted from enterohemorrhagic *Escherichia coli* (EHEC), a pathogen responsible for bloody diarrhea and hemolytic uremic syndrome (HUS) in humans. The invention relates to serodiagnostic techniques of these conditions using these proteins.

BACKGROUND OF THE INVENTION

The most common cause of bloody diarrhea and hemolytic uremic syndrome (HUS) in North America is infection by enterohemorrhagic *E. coli* (EHEC) (1). Alternative names for EHEC are Shiga toxin-producing *E. coli* (STEC), Shiga-like toxin-producing *E. coli* (SLTEC), Verocytotoxin-producing *E. coli* (VTEC), or Verotoxin-producing *E. coli*. In the United States, this food-borne *E. coli* is the most common infectious cause of bloody diarrhea in individuals of all ages. HUS is the most common cause of kidney failure in children in the U.S. and Canada.

This organism was the cause of the infamous "Jack-in-the-Box" food-poisoning outbreak in Seattle in 1993 which infected over 500 people and resulted in 4 deaths and many cases of long-term kidney damage. In 1996, this organism caused an enormous outbreak involving more than 8,000 people in Japan, resulting in 7 deaths. In late 1996, EHEC again caused an outbreak of food-poisoning in Scotland which affected 250 people and killed 18 people.

The most important virulence factor of *E. coli* associated with HUS is a potent cytotoxin known as Shiga toxin, Shiga-like toxin, verocytotoxin, or verotoxin, also called Stx. After production by *E. coli* colonizing the large intestine, Shiga toxin is absorbed into the circulation and eventually affects the kidney. The evidence linking Stx to HUS is both epidemiological and experimental. The first epidemiological association between Stx-producing *E. coli* and HUS was made by Karmali et al. (2) in 1983, and numerous studies since then have supported this association. Subsequent in vitro studies have shown that purified Stx has profound effects on renal endothelial cells resulting in cell death (3).

However, besides the clear-cut involvement of Stx in pathogenesis, little is known about other bacterial virulence factors involved in this disease. The lipopolysaccharide (LPS) of EHEC has been reported to enhance the effect of the Stx on human vascular endothelial cells (4), although the exact mechanism is not known. The other virulence factor of this organism that has been implicated in animal models is the 94 kilodalton outer membrane protein (OMP) known as intimin, which was discovered in the inventor's laboratory (5, 6). Intimin is involved in the colonization of the intestinal tract, which is apparently necessary for disease, but there is no evidence that intimin is directly involved in the renal disease. Since oral ingestion of preformed toxin is apparently not sufficient for causing HUS, other bacterial virulence factors clearly must be involved in the pathogenesis of this disease.

Two distinct sites of Disease, Intestinal and Renal

Disease due to EHEC starts by ingestion of meat, water, or other items that are contaminated with this organism. The organism then colonizes the large bowel where it can produce non-bloody diarrhea or bloody diarrhea (hemorrhagic colitis). In the colon, EHEC produces mucosal edema, erythema, ulceration and hemorrhage. A characteristic histopathology known as attaching and effacing (AE) results which is characterized by effacement of intestinal microvilli, intimate adherence of bacteria to enterocytes, and accumulation of polymerized actin and other cytoskeletal components in the epithelial cell directly beneath the adherent bacteria. The AE lesion has been repeatedly demonstrated in animals infected with EHEC and in cultured human epithelial cells. AE is assumed to occur in the colon early during the course of human infection, although direct evidence is lacking, probably because patients with EHEC infections undergo colonoscopy relatively late in the infection when the colonic surface has been denuded of epithelial cells. The AE histopathology is similar to that seen with enteropathogenic *E. coli* (EPEC), which do not produce Stx. We have shown that formation of the AE lesion by both EPEC and EHEC is mediated by the gene products of a 35 kilobase region of chromosomal DNA present in these strains but absent from normal flora *E. coli* (5, 7).

The pathogenic mechanisms by which EHEC produces non-bloody diarrhea and bloody diarrhea (hemorrhagic colitis) are largely unknown. Formation of the AE lesion in the absence of Stx is believed to be sufficient to cause non-bloody diarrhea in EPEC infections. Pure Stx can act as an enterotoxin, and in studies using rabbit jejunal tissue mounted in Ussing chambers, Stx selectively kills the absorptive tip cells while not affecting the secretory crypt cells, thereby changing the net balance of secretory/absorptive processes towards secretion (8). The bloody diarrhea is presumably due at least in part to the powerful cytotoxic effects of Stx, although the contribution of other bacterial factors and the host inflammatory response is not known. In at least two animal systems, gnotobiotic piglets and rabbits, Stx was not required for EHEC strains to alter secretory activity or cause severe histological changes (9, 10). O'Loughlin and colleagues (9, 11) have shown that disruption of colonic epithelium and changes in electrolyte transport during EHEC infection in rabbits are mediated by the host inflammatory response and that bacterial products other than Stx and factors encoded on the 60 MDa plasmid (see below) are necessary for the intestinal manifestations of EHEC disease.

The classic HUS triad includes microangiopathic hemolytic anemia, thrombocytopenia, and renal failure and may be accompanied by central nervous system manifestations in 30–50% of patients (12). Although hemolytic uremic syndrome (HUS) occurs in only 2–7% of all EHEC infections (while bloody diarrhea occurs in 90% of all infections (1,13)), HUS is associated with the greatest mortality due to this organism. The Shiga toxin produced in the bowel reaches the circulation and produces vascular endothelial damage that results in occlusion of the renal glomerular microvasculature by fibrin and platelets. Induction of inflammatory cytokines has also been suggested to contribute to the disease process (14–16). Although the preeminence of Stx in the disease process is accepted, the role of other bacterial factors in producing host damage or facilitating the delivery of Stx is unknown.

Virulence Factors of *E. coli* O157:H7

The majority of work on pathogenic factors of EHEC has focused on the Shiga toxins, which are encoded on bacteriophage inserted into the chromosome. Additional potential virulence factors are encoded in the chromosome and on a 60 MDa plasmid found in most strains of EHEC Toxins Stx occurs in two major forms, stx1 and Stx2, which share 55 and 57% sequence identity in the A and B subunits, respectively (17). While stx1 is highly conserved, sequence variation exists within Stx2. The toxins consist of a single A subunit of ca. 32 kDa and 5 identical B subunits of ca. 7.7 kDa (18) The B subunit serves to bind the toxin to a specific glycolipid receptor, globotriaosylceramide or $Gb_3$, while the A subunit is internalized and cleaves N-glycoside bonds on the 28S rRNA of the 60S ribosome. The resulting disruption of protein synthesis leads to death of renal endothelial cells, intestinal epithelial cells, vero or Hela cells, or any cell which possesses the $Gb_3$ receptor.

The 60 MDa plasmid commonly found in EHEC strains contains genes encoding an $\alpha$-hemolysin (19). Although this hemolysin is widely distributed among Stx-producing strains of *E. coli*, there are no data indicating that it is expressed in vivo or involved in pathogenesis of disease. Two other distinctly different phage-encoded hemolysins, termed enterohemolysins, are produced by many Stx-producing *E. coli* (20, 21) but again, there are no data to suggest in vivo expression or any role in pathogenesis.

Intestinal Adherence Factors

The only potential EHEC adherence factor which has been demonstrated to play a role in intestinal colonization in vivo in an animal model is the outer membrane protein intimin, encoded by the eaeA gene, also known as eae. We prepared an isogenic derivative of an EHEC strain specifically mutated in eaeA. In both conventional and gnotobiotic piglets (5, 22), a functional intimin protein was necessary for intimate adherence to intestinal epithelial cells, formation of the AE lesion, and induction of diarrhea. The importance of intimin in these processes was independently confirmed by other investigators using a different EHEC eaeA mutant in gnotobiotic piglets (23).

Other candidate adhesins have been reported but none have been well characterized or specifically demonstrated to play a role in adherence in vivo. Sherman et al. (24) reported that a 94 kDa OMP distinct from intimin (25) mediated adherence to Hep-2 epithelial cells, but no further characterization of this factor has been reported. Strains of EHEC produce fimbriae which might aid intestinal adherence (26–29), but no purified fimbriae or cloned fimbriae genes have been reported. An initial report (27) suggested that the 60 MDa plasmid was required for expression of fimbriae and adhesion to epithelial cells, but subsequent studies have reported that loss of the plasmid either enhanced adhesion (28), decreased adhesion (24), or had no effect on adhesion (29). The potential role of lipopolysaccharide (LPS) in adhesion was examined, and loss of LPS actually increased adherence to cultured epithelial cells (31). The existence of intestinal adherence factors distinct from intimin is suggested by the isolation of Stx-producing *E. coli* strains of serotypes other than EHEC that lack the eaeA gene but are still associated with bloody diarrhea or HUS in humans.

Other Potential Factors

LPS may either enhance or inhibit the toxicity of Stx in animal models (32,33) and enhances the cytotoxicity of Stx on human vascular endothelial cells in vitro (4). However, this effect is not specific for EHEC LPS since LPS from several species of the Enterobacteriaceae have similar effects (4). There is one report (34) that EHEC can invade cultured intestinal cell lines, but a later report (35) disputed these findings, showing that EHEC strains were no more invasive than normal flora *E. coli*. Furthermore, there is no in vivo evidence that invasion occurs in humans or in animals.

Non-O157:H7 STEC

Enterohemorrhagic *E. coli* O157:H7 is the most important type of *E. coli* that can cause HUS and bloody diarrhea. The O157:H7 nomenclature refers to particular bacterial surface antigens that define a serotype. The "O" designation refers to the surface lipopolysaccharide and the "H" antigen refers to the bacterial flagellar protein. Those *E. coli* that have the O157 and H7 antigens have the full array of virulence factors (Stx and intimin) and are always considered to be pathogens (36). However, there are similar *E. coli* that do not have the O157:H7 serotype but can cause similar disease. These *E. coli* are of serotypes such as O26:H11 and are called non-O157:H7 STEC (or non-O157:H7 EHEC). The major potential virulence factor that these organisms share is the Stx toxin but not all non-O157:H7 STEC are pathogenic (36). Mere expression of Stx alone does not define a pathogen. In fact, up to 63% of meat samples in U.S. supermarkets contain non-O157:H7 STEC (36). In contrast, *E. coli* O157:H7 is rarely found in foods. When non-O157:H7 STEC are isolated from patients, it is considered a pathogen but when they are isolated from food or animals, their significance is unknown (36). The invention described herein aids the discrimination of non-O157:H7 STEC that are of public health significance from those that are of little or no public health significance.

The reservoir of *E. coli* O157:H7 and non-O157:H7 STEC is believed to be in animals, particularly cattle (1). However, O157:H7 is rarely isolated from cattle, usually from less than 1% of cattle in most surveys (1). In contrast, non-O157:H7 STEC can be isolated from up to 40% of cattle (1). One important difference between non-O157:H7 STEC that are isolated from cattle and non-O157:H7 STEC isolated from humans is possession of the eae gene. The majority of these strains that are isolated from human disease possess the eae gene (37) whereas only a minority of these strains that are isolated from cattle possess eae and are presumably pathogenic for humans. Possession of the eae gene correlates with possession of a large block of virulence genes called the LEE (7) that also encode secreted proteins that are the basis of the present invention.

Serologic R

Determining the complete immune response to an infecting agent has many applications for understanding and controlling an infectious disease. First, such information can be used in serdiagnostics and seroepidemiology studies to detect evidence of an infection where the actual infectious agent cannot be detected either because of the lack of an appropriate specimen or lack of sufficiently sensitive detection methods. Second, knowledge of the components of an infectious agent which engender an immune response can be directly applied to developing a vaccine or immunotherapeutic agent (e.g., passive immunoglobulin). Third, detection of an immune response to a particular component of the infectious agent is direct evidence that this component is actually expressed in vivo during the course of infection, supporting the possibility that it plays a role in the pathogenesis of disease. The conclusion that an immune response indicates in vivo expression of the antigen is not always valid if, for example, the antigen is a toxin that is preformed at the time of ingestion or the infectious agent directly enters the blood stream without replication. However, for an agent that is ingested and replicates in the intestine, an immune response to a component strongly implies in vivo expression. For these reasons, a fuller determination of the immune response to *E. coli* O157:H7 is important for a better understanding of this disease.

Previous studies of the human immune response to *E. coli* O157:H7 have focused on the serological response since there is no evidence that cell-mediated immunity plays a role in this disease. The most widely studied antigen is the LPS. Chart et al. (38) showed that in one study of 60 patients with HUS, Stx or a Stx-producing *E. coli* could be detected in only $^{23}$% of fecal specimens whereas an IgM response to the O157 LPS was detected in 73% of these patients. In an epidemic situation, an immunoassay based on IgG responses to LPS was over 90% sensitive and specific for patients with recent culture-confirmed infection (39). Antibodies to the other antigen of the O157:H7 serotype, the H7 flagella, were not detected in any of the HUS patients studied by Chart et al. (40). In this same study, some patients showed responses to outer membrane proteins (OMPs) but this response was found to be due to contaminating LPS co-migrating with the OMPs.

Stx represents an obvious choice for an important antigen produced in vivo. However, numerous investigations of the serological response to Stx have yielded disappointing results. A curious phenomenon is that sera from most individuals without any history of infection with Stx-producing *E. coli* contain a substance that is capable of neutralizing Stx2. When ELISA rather than neutralization tests are conducted to detect antibodies against either Stx1 or Stx2, only a minority of HUS patients showed a response to these toxins (39, 41–43). Similar results are seen in patients infected with Stx-producing *Shigella dysenteriae* type (44) and may be related to the fact that Stx is cytotoxic to human B lymphocytes (45). Whatever the reason, these results have led experts to conclude that antitoxin response is not a useful tool in the serodiagnosis of Stx-producing *E. Coli* (39, 41, 42, 46)

Serological responses to *E. coli* O157:H7 and non-O157:H7 STEC in cattle have not been as extensively studied as in humans. Some cattle experimentally infected with *E. coli* O157 developed serum antibodies against Stx and O157 LPS but others did not (55). Detection of antibodies against Stx in cattle is not useful in predicting the potential for human disease since the prevalance of non-O157:H7 STEC of doubtful pathogenic significance is so high in cattle, as described above.

In summary, several years of research into the pathogenesis and immune response of *E. coli* O157:H7 infections have not yielded firm knowledge of the protective immune response or an ideal serodiagnostic tool. The O157 LPS is useful for serodiagnosis, but it is difficult to prepare and the response may be nonspecific since O157 LPS shares epitopes with *E. coli* O44 LPS (43) and the LPS of certain serogroups of Salmonella spp., *Yersinia enterocolitica*, *Brucella abortus*, and *Vibrio cholerae* non-O1 strains (reviewed in (47). It is also useless for detecting infection due to Stx-producing *E. coli* strains of non-O157 serogroups. On the other hand, Stx is clearly produced in vivo and is essential for disease, but is not useful for serodiagnosis.
Summary Although extensive research has been conducted on the Shiga toxins expressed by this organism, there is very little known about other potential virulence factors of this pathogen. There is clearly a need in the art to have definitive diagnostic techniques available. We have discovered novel proteins that are secreted by Stx-producing strains of *E. coli* serotypes O157:H7 and O26:H11. These proteins are expressed during the course of infection and are highly immunogenic in humans, and is therefore useful as serodiagnostic tool. Furthermore, these proteins are also immunogenic in cattle. The invention teaches a method for determining cattle which are infected with EHEC. Cattle which test positive can be omitted from food production.

SUMMARY OF THE INVENTION

It is the object of the invention to provide proteins which are secreted from EHEC, are called Esp, and trigger a strong immune response in a subject.

It is another object of the invention to provide a 37 kilodalton protein (EspB) secreted from *E. coil* O157:H7.

It is another object of the invention to provide a 24 kilodalton protein (EspA) secreted from *E. coil* O157:H7.

It is another object of the invention to provide genes which encode the secreted Esp proteins from *E. coil* O157:H7.

It is a further object of the invention to provide a serodiagnostic test such as an ELISA or a Western blot for determining the presence of the secreted Esp proteins in a subject, wherein the subject can be a human or a cow.

It is a still a further object of the invention to provide a test kit for both humans and cows which with the use of a substrate coated with the secrected Esp proteins, will diagnose the presence of antibodies to the *E. coli* secreted Esp proteins in said human or cow almost instantaneously.

BRIEF DESCRIPTION OF THE DRAWINGS

FIG. 1: Coomasie blue-stained SDS/polyacylamide gel (1A) and identical immunoblot probed with rabbit antiserum against EPEC secreted proteins (B) of culture supernatants from EHEC strains 84-289 [O157:H7] (lane 1), 85-170 [O157:H7] (lane 2), 86-24 [O157:H7] (lane 3), EDL933 [O157:H7] (lane 4), NF4 [O157:H7] (lane5), 83-574 [O26:H11](lane 6), 6549 [O26:H11] (lane 7), EPEC E2348/69 (lane 8), and *E. coil* HS-4 (lane 9).

DETAILED DESCRIPTION OF THE INVENTION

Enterohemorrhagic *E. coli* are the most common cause of hemorrhagic colitis, a bloody diarrhea which can lead to life threatening hemolytic uremic syndrome (HUS) (1, 2). Infections caused by EHEC and another diarrheagenic pathogen, enteropathogenic *E.coli* (EPEC) result in a histopathology called attaching and effacing (AE) (5, 22, 48).

Another feature common to both EPEC and EHEC is the presence of a large chromosomal locus called the LEE (Locus for Enterocyte Effacement) which encodes all of the known virulence factors necessary for AE lesions (7). One gene within the LEE, eaeA (*E.coli* attaching and effacing), encodes an outer membrane protein called intimin which is required but not sufficient for AE lesion formation (5, 48, 49). Two other genes within the EPEC LEE, espA, encoding a 25 kilodalton polypeptide (50) and espB (formerly called eaeB) encoding a 37 kilodalton polypeptide (51) are necessary for epithelial cell signal transduction events during AE lesion formation (52). The espA and espB gene products are secreted to the culture supernatant during in vitro growth and are presumed to interact with host cells during natural infections (53,54). When the espB gene is present, the eae genes are also present (7). A transport apparatus that secretes the Esp proteins and several other polypeptides is also encoded by genes in the EPEC and EHEC LEE (53).

The strain of EHEC used in the invention is not specifically important. The *E. coli* O157:H7 was chosen for the majority of studies since this is the most common serotype implicated in disease in North America. However results obtained with O157:H7 can be related to other serotypes of Stx-producing *E. coli* strains since non-O157:H7 serotypes are more prominent outside of North America. Strains used in this study are included in Table 1.

Enterohemorrhagic *E. coli* strains secrete proteins in addition to Stx antigens, but such antigens are previously undescribed. These proteins are produced in vivo during infection. Several of these proteins are secreted from the bacterial cells by a specialized protein secretion system homologous to the secretion systems involved in secretion of crucial virulence factors by Shigella, Salmonella, and Yersina species. These proteins have been purified sufficiently to be employed in serological assays. This data demonstrates that a stong immunological response is produced in humans and cows. The antibodies are detected via Western blot and ELISA.

To obtain large quantities of highly purified protein, the genes encoding these highly antigenic proteins were sequenced. The choice of method used to clone the genes which encode the antigenic proteins is not crucial. Well-known methods in the art could be employed. For example, the preferred method of the invention is the Polymerase Chain Reaction (PCR). For example, the primer sequences used in the PCR reaction for the espB gene are as follows:

K-638,5'-
CCATTTGCTCTTCCGCACCCAGCTAAGCGACC (SEQ ID No.1);

K-639,
5'-TCCGACGCATATGAATACTATTGATAATACT (SEQ ID No. 2).

PCR primers were designed using homologous gene sequences which encode secreted proteins from EPEC (51, 52). Restriction sites for Nde I and Sap I were incorporated into the 5' and 3' ends of espB respectively. The gene for the 37 kilodalton protein from EHEC was cloned using this method. Subsequent cloning and expression was accomplished using standard methods in the art.

The purification method used to isolate the recombinant proteins is not crucial to the invention. Any known method can be used to isolate and sufficiently purify the recombinant protein of interest. Such methods are known in the art. For example, the preferred embodiment is the IMPACT system (New England Biolabs). This system allows the recombinant protein to be readily purified by column chromatography, however, one of ordinary skill in the art would know appropriate protein purification techniques which can also be used.

Using these standard procedures, the gene encoding the 37 kilodalton protein, also known as EspB was cloned and sequenced. The gene sequence which encodes the EspB protein as shown is as follows:

(SEQ ID #4)
```
             10                  30                  50
ATGAATACTATTGATAATACTCAAGTAACGATGGTTAATTCCGCTTCGGAGAGTACGACC
 M  N  T  I  D  N  T  Q  V  T  M  V  N  S  A  S  E  S  T  T 70                  90                 110
GGCGCTTCCAGTGCAGTTGCCGCATCTGCTTTATCAATTGATTCATCTCTGCTTACTGAT
 G  A  S  S  A  V  A  A  S  A  L  S  I  D  S  S  L  L  T  D 130                 150                 170
GGTAAGGTTGATATTTGTAAGCTGATGCTGGAAATTCAAAAACTCCTCGGCAAGATGGTG
 G  K  V  D  I  C  K  L  M  L  E  I  Q  K  L  L  G  K  M  V 190                 210                 230
ACTCTATTGCAGGATTACCAACAAAAACAATTGGCGCAAAGCTATCAGATTCAGCAGGCC
 T  L  L  Q  D  Y  Q  Q  K  Q  L  A  Q  S  Y  Q  I  Q  Q  A 250                 270                 290
GTTTTTGAGAGCCAGAATAAAGCTATTGAGGAAAAAAAAGCCGCGGCAACCGCTGCTTTG
 V  F  E  S  Q  N  K  A  I  E  E  K  K  A  A  A  T  A  A  L 310                 330                 350
```

```
                                -continued
GTTGGCGGGATTATTTCATCAGCATTGGGGATCTTAGGTTCTTTTGCAGCAATGAACAAC
 V  G  G  I  I  S  S  A  L  G  I  L  G  S  F  A  A  M  N  N 370               390               410
GCGGCTAAAGGGGCTGGTGAGATTGCTGAAAAAGCAAGCTCTGCATCTTCAAAGGCTGCT
 A  A  K  G  A  G  E  I  A  E  K  A  S  S  A  S  S  K  A  A 430               450               470
GGTGCGGCTTCTGAGGTTGCAAATAAAGCTCTGGTCAAGGCTACGGAAAGTGTTGCTGAT
 G  A  A  S  E  V  A  N  K  A  L  V  K  A  T  E  S  V  A  D 490               510               530
GTCGCAGAGGAGGCATCCAGTGCGATGCAGAAAGCGATGGCCACAACAACGAAAGCAGCC
 V  A  E  E  A  S  S  A  M  Q  K  A  M  A  T  T  T  K  A  A 550               570               590
AGCCGTGCATCTGGCGTTGCAGATGATGTTGCGAAAGCCTCTGACTTTGCTGAAAATCTT
 S  R  A  S  G  V  A  D  D  V  A  K  A  S  D  F  A  E  N  L 610               630               650
GCAGACCCCGCCGAGAAGACAAGCAGAATCAATAAGTTGTTGAATTCCGTAGATAAACTG
 A  D  P  A  E  K  T  S  R  I  N  K  L  L  N  S  V  D  K  L 670               690               710
ACCAATACCACAGCATTTGTTGCCGTGACCAGTCTTGCTGAAGGTACGAAAACGTTGCCA
 T  N  T  T  A  F  V  A  V  T  S  L  A  E  G  T  K  T  L  P 730               750               770
ACAACAATATCTGAGTCCGTCAAATCGACTCATGAGGTTAATGAACAACGTGCGAAGTCG
 T  T  I  S  E  S  V  K  S  T  H  E  V  N  E  Q  R  A  K  S 790               810               830
CTGGAAAACTTCCAGCAGGGGAATCTGGAGCTGTATAAACAAGACGTTCGCAGAACGCAG
 L  E  N  F  Q  Q  G  N  L  E  L  Y  K  Q  D  V  R  R  T  Q 850               870               890
GATGATATCACGACTCGTCTGCGTGATATAACGTCCGCTGTCCGCGATCTCCTTGAGGTC
 D  D  I  T  T  R  L  R  D  I  T  S  A  V  R  D  L  L  E  V 910               930
CAGAATCGTATGGGGCAATCGGGTCGCTTAGCTGGGT
 Q  N  R  M  G  Q  S  G  R  L  A  G
```

The antigenic proteins induce antibodies in HUS patients. The 24, 37, and 110 kilodaltons are the most consistently seen, and represent the three seemingly most antigenic proteins in the strains studied. The 37 kilodalton protein is also known as EspB; the 24 kilodalton is known as EspA These proteins are the most preferred embodiments for use in the invention.

Western immunoblots and enzyme-linked immunosorbent assays (ELISA) were used to identify the serodiagnostic capabilities of the newly discovered secreted antigens from EHEC. Briefly, Western blots were done as follows. The antigen (either 37 or 24 kilodalton) sample is separated in an analytical gel, for example an SDS polyacrylamide gel or an isoelectric focusing gel. The resolved molecules are transferred electrophoretically to a nitrocellulose membrane in a blotting tank. The blot is then treated sequentially with serum collected from a subject, and washed, and then a radiolabelled or chemiluminescent conjugate to detect antibodies is bound to the blot. After washing again, the blot is placed in contact with X-ray flm in a cassette; the autoradiograph is developed and the antigen bands which have bound the antibody are visible.

ELISA assays were performed as follows. The antigen in saline is incubated on a plastic plate, and small quantities become absorbed onto the plastic surface. Free antigen is washed away. The plate may then be blocked with excess of an irrelevant protein to prevent any subsequent non-specific binding of proteins. Test antibody is added, which binds to the antigen. Unbound proteins are washed away and a ligand is added which can detect the antibody and is covalently coupled to an enzyme such as peroxidase. The bound ligand is visualized by the addition of an enzymatic substrate, which acts as a colored indicator.

Figure 4:
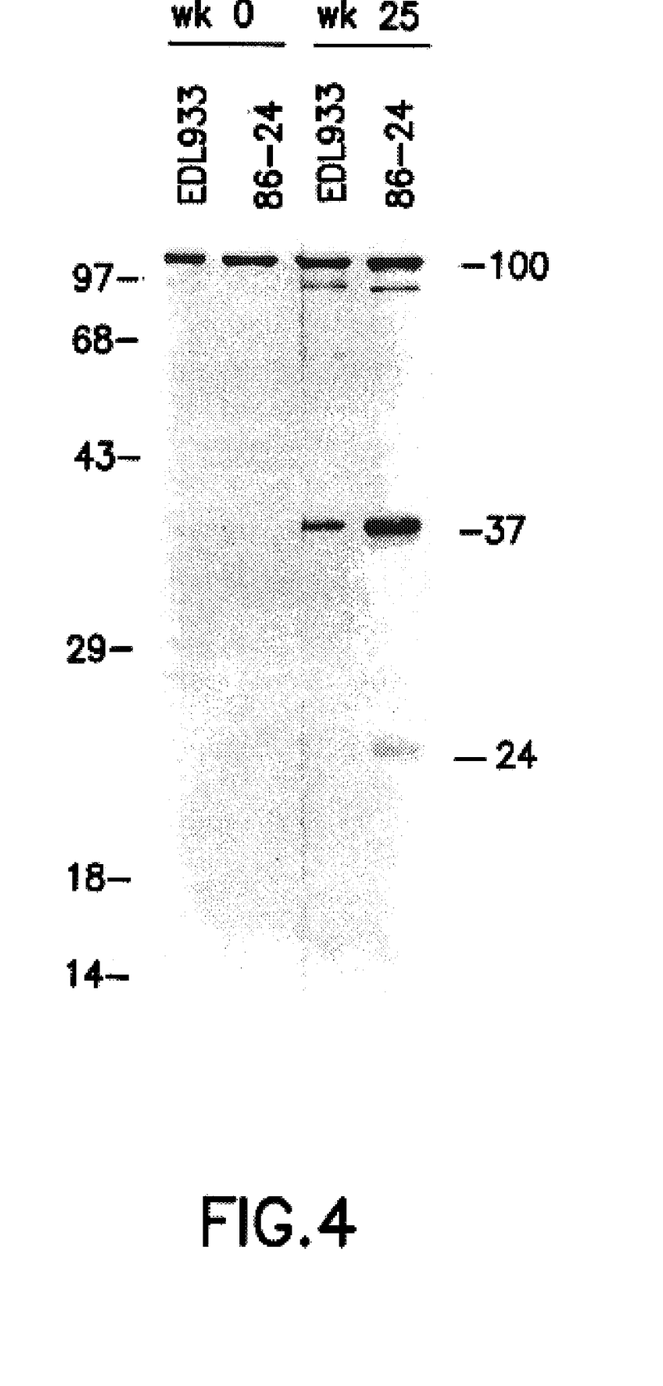
FIG. 4: Western immunoblot using serum from a cow prior to experimental infection with *E. coli* O157:H7 strains EDL933 and 86-24. Secreted Esp proteins from EDL933 and 86-24 strains were used as antigens and 25 weeks post-infection.
Figure 5:
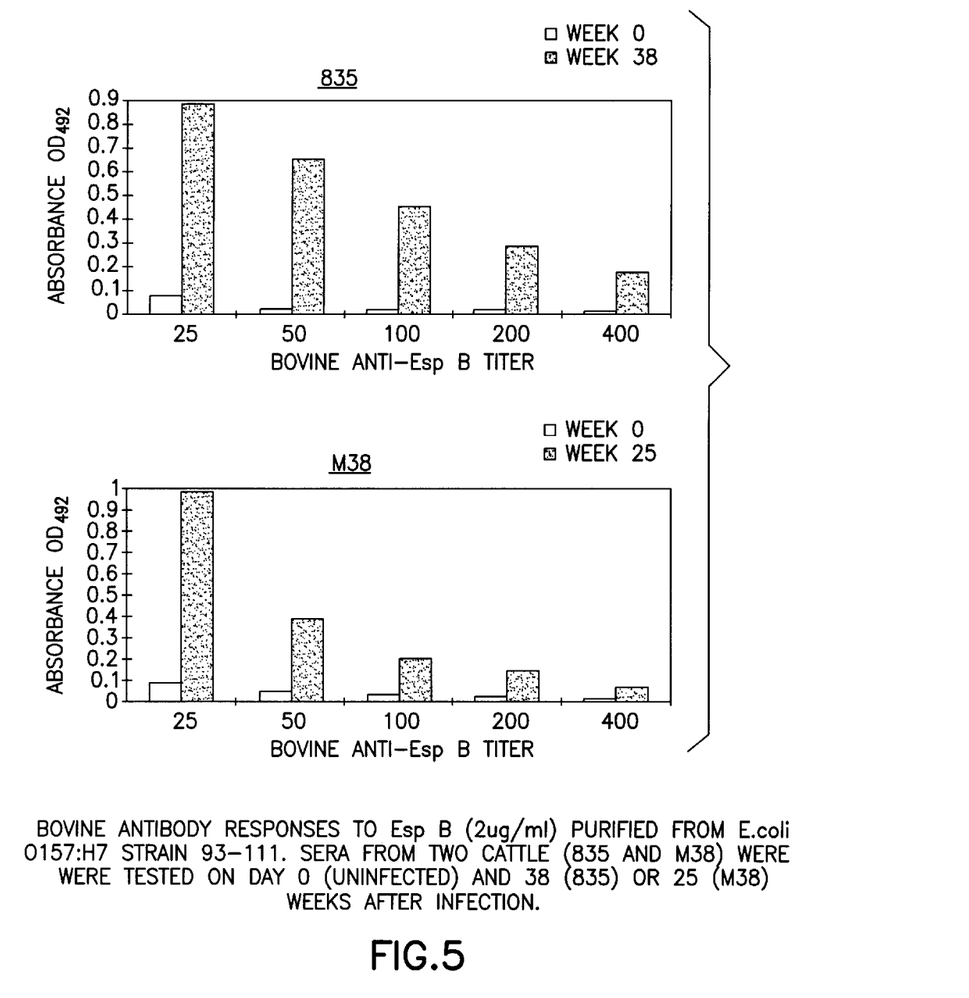
FIG. 5: Bovine antibody responses to EspB (2 μg/ml) purified from *E. coil* O157 strain 93-111. Sera from two cattle (835 and M38) were tested on day 0 (uninfected) and 38 (835) or 25 (M38) weeks after infection.

Sera from cows experimentally infected with E. coli 0157:H7 were examined (55). As is extensively documented in the literature, cows are the major reservoir of this pathogenic bacteria and people become ill from eating insufficiently cooked hamburgers or vegetables which have come in contact with cow feces. However, there is no reliable way to determine which cows have this pathogen in their intestinal tract. Simple bacteriologic examination of feces is very insensitive. The invention demonstrates that when cows harbor this organism in their intestine they develop antibodies to the secreted proteins. Western immunoblot using serum from a cow that was collected before experimental infection with E. coli 0157:H7 (day 0 serum) and serum collected from the same cow 25 or 38 weeks after infection. The immunoblot shows that there are no antibodies at day 0, but there is a strong antibody resonse to these proteins 25 or 38 weeks after infection.

A test kit is envisioned to test beef cows in a herd. Cows which are positive would not then be used to make hamburger or other foods for human consumption. The purified 37 kilodalton protein could be used in a test where the presence of antibodies could turn an indicator a certain color. Any kind of substrate could be used. The substrate, such as filter paper would contian secreted Esp protein. Serum would be added to the substrate and a color indicator. A color indicator could be used to detect the presence of antibodies in a sample of serum from a subject. Different kits would be developed for cow and human sera.

The following examples are provided for illustrative purposes only, and are in no way intended to limit the scope of the present invention.

EXAMPLE 1

Secretion of Proteins of *E. coli* 0157:H7

*E.coli* 0157:H7 were grown in 100ml of Eagles's minimal medium at 37° C. shaking to mid-log ($OD_{600}$ of 1.0). Bacteria were pelleted by centrifugation (10,000×g, 10 min.) and phenylmethylsulfonyl fluoride (PMSF, 50 ug/ml), aprotinin (0.5 ug/ml) and EDTA (0.5 uM) were added to the supernatants to inhibit digestion by proteases. After passage through 0.45 um filters, the culture supernatants were concentrated 100 fold in Omegacell disposable stirred cell filtration devices (Filtron Technology, Northborough, Mass.). Samples were then run on SDS-PAGE gels and stained (Millipore) and processed for immunoblots as previously described (53).

Samples were analyzed by SDS-PAGE or western immunoblot using rabbit antiserum (diluted 1:1000) raised against EPEC secreted proteins or human serum (diluted 1:1000) from an individual who developed HUS subsequent to an 0157:H7 EHEC infection.

EXAMPLE 2

Detection of EHEC Secreted Proteins with EPEC Antiserum

Figure 1A:
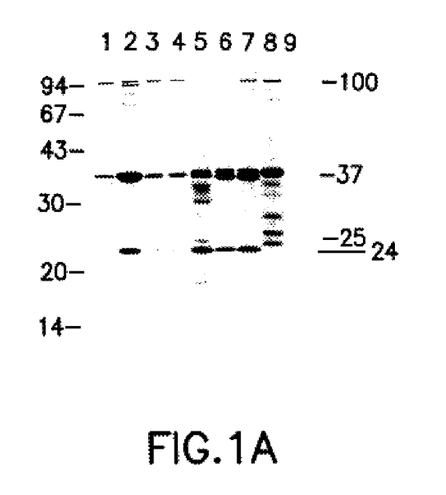
Figure 1B:
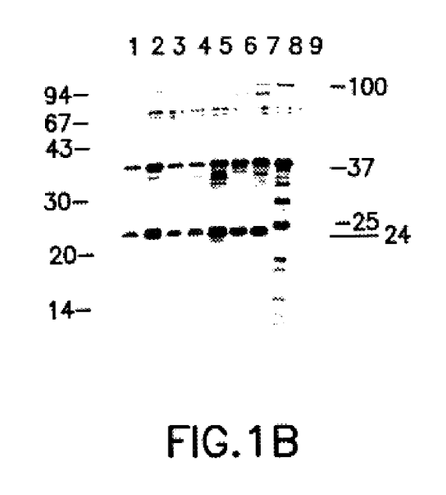

Six EHEC strains were tested for the presence of secreted proteins using antiserum raised against EPEC secreted proteins. FIGS. 1A and 1B shows an SDS PAGE and an identical western immunoblot of the secreted proteins from five 0157:H7 stains (lanes 1–5) and two 026:H11 strains (lanes 6–7). Culture supernatants from EPEC strain E2348/69 (Lane 8) and *E. coli* HS-4 (lane 9), an avirulent fecal isolate, are shown for comparison. All of the EHEC secrete 100-110, 37- and 24-kilodalton polypeptides with the exception of 6549 which does not secrete the 100-110 kilodalton protein.

EXAMPLE 3

Detection of EHEC Secreted Proteins with HUS Human Serum

Figure 2:
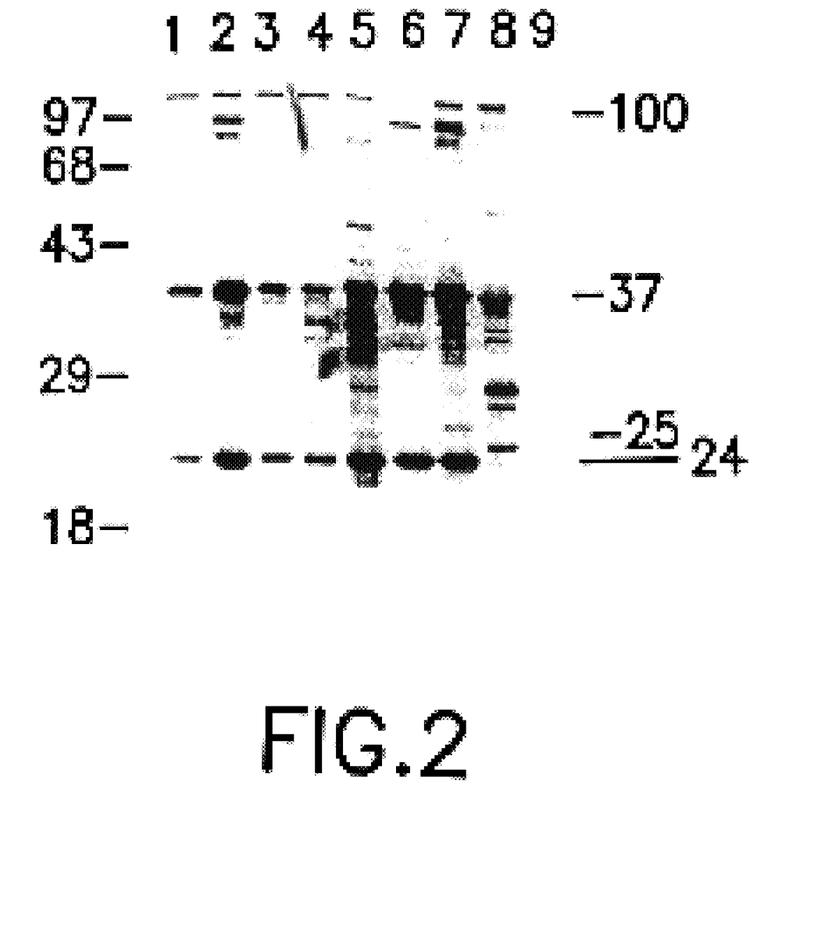
FIG. 2: Immunoblot or culture supernatants from EHEC strains 84-289 [O157:H7] (lane 1), 85-170 [O157:H7] (lane 2), 86-24 [O157:H7] (lane 3), EDL933 [O157:H7] (lane 4), NF4 [O157:H7] (lane 5), 83-574 [O26:H11] (lane 6), 6549 [O26:H11](lane 7), EPEC E2348/69 (lane 8, and *E. coli* HS-4) probed with human serum from a patient who developed HUS.
Figure 6:
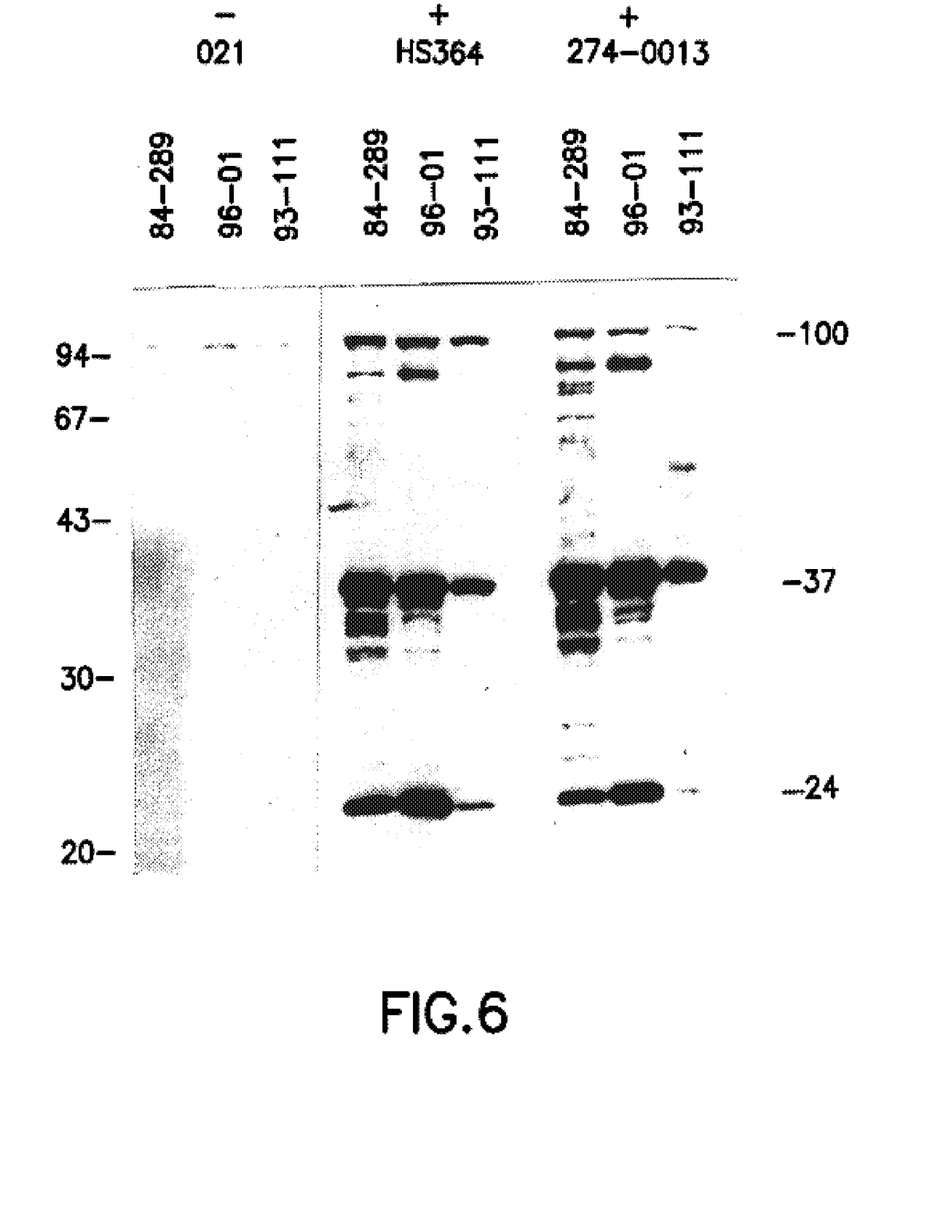
FIG. 6: Immunoblot of culture supernatants from 84-289, 93-111, and 96-01 probed with human antiserum from an uninfected child (O21), and HUS positive patient from the 1993 Washington state outbreak (HS364), and a patient from an isolated case of HUS (274-0013). The antisera were diluted 1:10,000.

Westerm immunoblot analysis was performed to determine whether the secreted proteins are present in human serum collected from a patient who developed HUS as a result of an 0157:H7 EHEC infection. FIG. 2 shows that the EHEC secreted proteins are recognized by human serum and that the recognition pattern is similar to that seen with rabbit antiserum against EPEC secreted proteins. All of the strains secrete polypeptides of 37- and 24-kilodaltons that are recognized by the human serum from an HUS patient but not with serum from uninfected children. The results are presented in FIG. 6.

EXAMPLE 4

Immunoblot of Secreted EHEC Proteins Probed with Serum From HUS+/− Patients

Figure 3A:
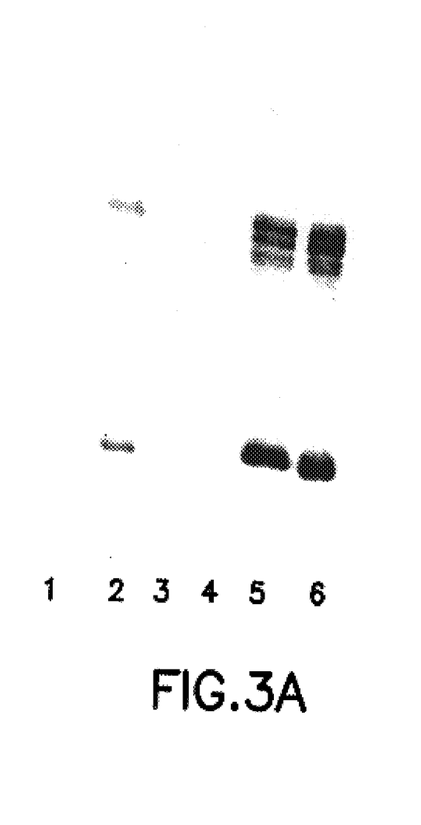
FIG. 3: Immunoblot of secreted EHEC proteins probed with sera collected from a patient (HS363) infected with O157:H7 without HUS (panel A) and a patient (HS364) infected with O157:H7 with HUS (panel B). Lanes: [1]86-24 (O157:H7); [2]84-289 (O157:H7); [3]933 (O157:H7); [4] NF4 (O157:H7); [5]83-574 (O26:H11); [6]6549 (O26:H11). Sera (both diluted 1:5000 final) were reacted to identical blots with equal loadings of antigen.
Figure 3B:
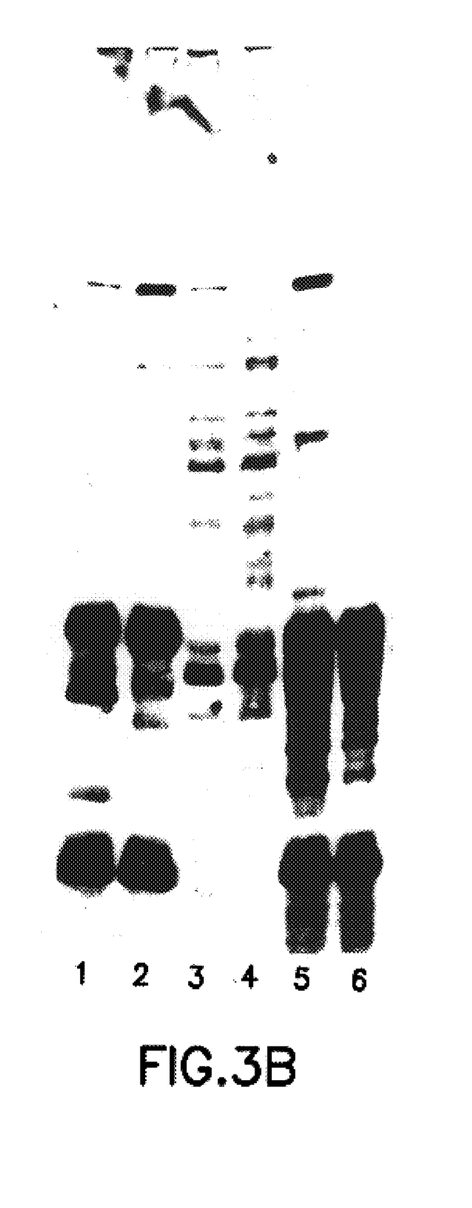

Sera was screened from 6 patients infected with *E. coli* 0157:H7 during the 1993 Washinton State outbreak. Of these 6 sera, 3 were from children with HUS and 3 were from children infected with 0157:H7 and had diarrhea but no HUS. With some serum samples, we can dilute the sera to greater than 1:100,000 and still see a clear response to these secreted EHEC proteins. An example of this is shown in FIG. 3 in which secreted proteins from the identical panel of strains were immunoblotted with serum from an HUS-negative child (panel A) and from an HUS-positive child (panel B).

EXAMPLE 5

Cloning of espB Gene From *E. coli* 0157:H7

The espB gene of *E. coli* 0157:H7 strain 93-111 (encoding 37 kilodalton protein) was generated using the polymerase chain reaction with restriction sites that allowed the gene to be cloned into a vector pCYB1 from the IMPACT I, One Step protein Purification System (New England Biolabs). The primer sequences used for PCR were as follows:

K-638,
5'-CCATTTGCTCTTCCGCACCCAGCTAAGCGACC (SEQ ID No. 1);

K-639,
5'-TCCGACGCATATGAATACTATTGATAATACT (SEQ ID No. 2).

PCR primers were designed using homologous gene sequences which encode secreted proteins from EPEC. Restriction sites for Nde I and Sap I were incorporated into the 5' and 3' ends of espB respectively. The sequence of the PCR product was confirmed using the above primers to sequence the DNA before cloning. After the gene was cloned into pCYB1 it was sequenced again using the universal vector primers NEB #1260 and NEB #1261 supplied with the IMPACT kit.

EXAMPLE 6

Purification of the espB Protein

The IMPACT I Intein Mediated Purification with an Affinity Chitin-binding Tag is a protein purification system that allows the cloning of genes into vectors supplied with the kit to generate a three part gene fusion (C-terminal) which can be over expressed by inducing a tac promotor with IPTG (0.5 mM) and then purified. The gene of interest, the gene encoding the 37 kilodalton (espB) is cloned into the appropriate vector so that it is in frame with an Intein moiety and a chitin binding domain (CBD). The vectors are under the control of the ptac promotor which enables IPTG induced expression of the fusion protein. The induced bacterial culture is then lysed by a French Press and the extract containing EspB-intein-CBD-fusion is added to a column containing chitin beads. The EspB protein is then cleaved from the fusion with dithiothreitol (30 mM) and eluted from the column. The dithiothreitol was removed by dialysis against phosphate buffered saline (4 times 4 liters) and concentrated with Centricon concentrators (Amicon).

N-terminal sequencing of the EspB protein (37 kilodalton) was determined by the Edman degradation procedure. The first four amino acids of the 37 kilodalton from the EHEC strain 84-289 supernatants are Met-Asn-Thr-Ile (SEQ ID No. 3).

EXAMPLE 7

Western Immunoblot Using Infected Cow Sera

Western immunoblots prepared according to the procedure outlined in Example 1 were used with serum from a cow that was collected before experimental infection with *E. coli* 0157:H7 (day 0 serum) and serum from the same cow collected 25 weeks after infection (55). The results are presented in FIG. 4. The two different gel lanes labeled EDL933 and 86-24 are antigens prepared from two different strains of *E. coli* O157:H7, EDL933 and 86-24.

EXAMPLE 8

Enzyme-Linked Immunosorbent Assay (ELISA)

Sera was obtained from two cows that had been experimentally infected with *E. coli* O157:H7. From one cow, sera from week 0 (before infection) and week 38 (after infection are shown. From the other cow, sera from week 0 and week 25.

Immulon-II (Dynatech) plates were coated overnight with 100 ul of purified EspB (2 ug/ml) in phosphate buffered saline (PBS). Control wells contain an equal volume of PBS. The plates were washed three times with PBS and unbound sites were blocked with 6% bovine serum albumin, 0.05% Tween by incubation for one hour at room temperature. Plates were incubated for 1 hour at 37° C. with dilutions of the following sera: Bovine M38 Day 0, M38 25 weeks after infection, 835 Day 0, 835 38 weeks post-infection. Bovine anti-EspB responses were detected with a goat anti-bovine horseradish peroxidase conjugate (1:5000). The conjugate incubations were for 1 hour at 37° C. in PBS/Tween. The secondary antibodies were removed by washing and antibody responses detected with the appropriate substrate solution for 30 minutes and read at the appropriate wavelength on an ELISA plate reader. Data represent the mean of duplicate antibody dilutions after subtracting the values of the negative control wells.

FIG. 5 shows different dilutions of the cow sera on the bottom axis. The white bar is the absorbance from week 0 sera and the black bar is the absorbance at week 25 or 38. Even diluting the cow sera to 1:200, there is still a clear-cut difference between the pre- and post-infection titers.

EXAMPLE 9

Human Antibody Responses Using an ELISA Test

Figure 7:
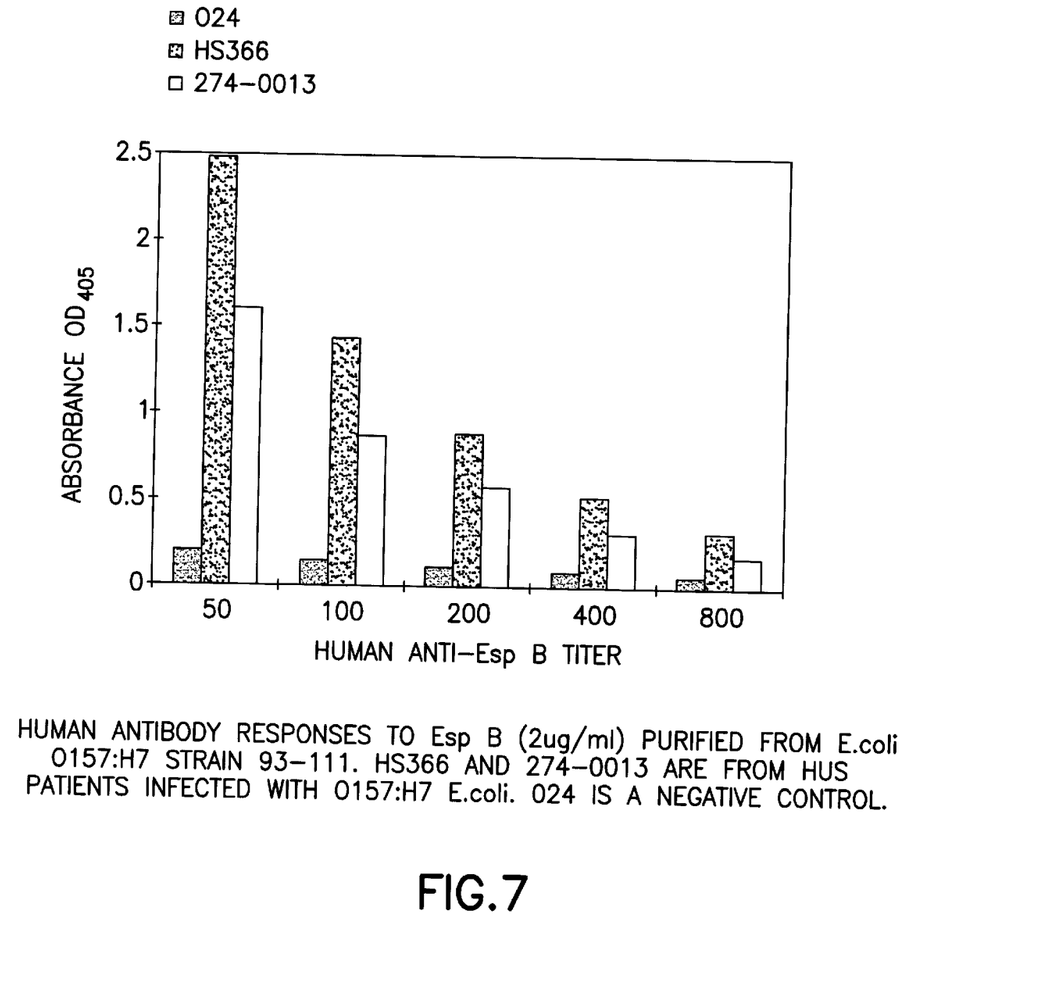
FIG. 7: Human antibody responses to EspB (2 μg/ml) purified from O157:H7 E.coli. strain 93-111. HS366 and 274-0013 are from HUS patients infected with O157:H7 E.coli. 024 is a negative control.

Sera was obtained from two HUS patients infected with O157:H7 *E.coli*. EspB (2 ug/ml) were purified from *E.coli* O157:H7 strain 93-111. HS366 and 274-0013 are from HUS patients infected with O157:H7 *E.coli*. Procedures were followed as in example 8. Results are shown in FIG. 7.

REFERENCES

1. Griffin, P. M. and R. V. Tauxe. 1991. The epidemiology of infections caused by *Escherichia coli* O157:H7, other enterohemorrhagic *E. coli*, and the associated hemolytic uremic syndrome. Epidemiol. Rev. 13:60–98.
2. Karmali, M. A., B. T. Steele, M. Petric, and C. Lim. 1983. Sporadic cases of haemolytic uremic syndrome associated with faecal cytotoxin and cytotoxin-producing *Escherichia coli* in stools. Lancet i:619–620.
3. Louise, C. B. and T. G. Obrig. 1995. Specific interaction of *Escherichia coli* O157:H7-derived Shiga-like toxin II with human renal endothelial cells. J. Infect. Dis. 172:1397–1401.
4. Louise, C. B. and T. G. Obrig. 1992. Shiga toxin-associated hemolytic uremic syndrome: combined cytotoxic effects of Shiga toxin and lipopolysaccharide (endotoxin) on human vascular endothelial cells in vitro. Infect. Immun. 60:1536–1543.
5. Donnenberg, M. S., S. Tzipori, M. L. McKee, A. D. O'Brien, J. Alroy, and J. B. Kaper. 1993. The role of the eae gene of enterohemorrhagic *Escherichia coli* in intimate attachment in vitro and in a porcine model. J. Clin. Invest. 92:1418–1424.
6. Yu, J. and J. B. Kaptr. 1992. Cloning and characterization of the eae gene of enterohaemorrhagic *Escherichia coli* O157:H7. Mol. Microbiol. 6:411–417.
7. McDaniel, T. K., K. G. Jarvis, M. S. Donnenberg, and J. B. Kaper. 1995. A genetic locus of enterocyte effacement conserved among diverse enterobacterial pathogens. Proc. Natl. Acad. Sci. USA 92:1664–1668.
8. Kandel, G., A. Donohue-Rolfe, M. Donowitz, and G. T. Keusch. 1989. Pathogenesis of Shigella diarrhea XVI. Selective targetting of shiga toxin to villus cells of rabbit jejunum explains the effect of the toxin on intestinal electrolyte transport. J. Clin. Invest. 84:1509–1517.
9. Li, Z., C. Bell, A. Buret, R. Robins-Browne, D. Stiel, and E. O'Loughlin. 1993. The effect of enterohemorrhagic *Escherichia coli* O157: H7 on intestinal structure and solute transport in rabbits. Gastroenterol. 104:467–474.
10. Tzipori, S., H. Karch, I. K. Wachsmuth, R. M. Robins-Browne, A. D. O'Brien, H. Lior, M. L. Cohen, J. Smithers, and M. M. Levine. 1987. Role of a 60-megadalton plasmid and Shiga-like toxins in the pathogenesis of infection caused by enterohemorrhagic *Escherichia coli* O157:H7 in gnotobiotic piglets. Infect. Immun. 55:3117–3125.
11. Elliott, E., Z. Li, C. Bell, D. Stiel, A. Buret, J. Wallace, I. Brzuszczak, and E. O'Loughlin. 1994. Modulation of host response to *Escherichia coli* O157:H7 infection by anti-CD18 antibody in rabbits. Gastroenterol. 106:1554–1561.
12. Su, C. and L. J. Brandt. 1995. *Escherichia coli* O157:H7 infection in humans. Ann. Intern. Med. 123:698–714.
13. Tarr, V. 1. 1995. *Escherichia coli* O157:H7: Clinical, diagnostic, and epidemiological aspects of human infection. Clin. Infect. Dis. 20:1–10.
14. Van de Kar, N. C. A. J., L. A. H. Monnens, M. A. Karmali, and V. W. M. Van Hinsbergh. 1992. Tumor necrosis factor and interleukin-1 induce expression of the verotoxin receptor globotriaosylceramide on human endothelial cells: implications for the pathogenesis of the hemolytic uremic syndrome. Blood 80:2755–2764.
15. Tesh, V. L., B. Rarrmegowda, and J. E. Samuel. 1994. Purified Shiga-like toxins induce expression of proinflammatory cytokines from murine peritoneal macrophages. Infect. Immun. 62:5085–5094.
16. Louise, C. B. and T. G. Obrig. 1991. Shiga toxin-associated hemolytic uremic syndrome: combined. cytotoxic effects of Shiga toxin, interleukin-1, and tumor necrosis factor alpha on human vascular endothelial cells in vitro. Infect. Immun. 59:4173–4179.
17. Jackson, M. P., R. J. Neill, A. D. O'Brien, R. K. Holmes, and J. W. Newland. 1987. Nucleotide sequence analysis and comparision of the structural genes for Shiga-like toxin I and Shiga-like toxin II encoded by bacteriophages from *Escherichia coli* 933. FEMS Microbiol. Lett. 44:109–114.
18. Tesh, V. L. and A. D. O'Brien. 1991. The pathogenic mechanisms of Shiga toxin and the Shiga-like toxins. Molec. Microbiol. 5:1817–1822.
19. Schmidt, H., L. Beutin, and H. Karch. 1995. Molecular analysis of the plasmid-encoded hemolysin of *Escherichia coli* O157:H7 strain EDL 933. Infect. Immun. 63:1055–1061.
20. Stroeher, U. H., L. Bode, L. Beutin, and P. A. Manning. 1993. Characterization and sequence of a 33-kDa enterohemolysin (Ehly1)-associated protein in *Escherichia coli*. Gene 132:89–94.
21. Beutin, L., U. H. Stroeher, and P. A. Manning. 1993. Isolation of enterohemolysin (Ehly2)-associated sequences encoded on temperate phages of *Escherichia coli*. Gene 132:95–99.

22. Tzipori, S., F. Gunzer, M. S. Donnenberg, L. deMontigny, J. B. Kaper, and A. Donohue-Rolfe. 1995. The role of the eaeA gene in diarrhea and neurological complications in a gnotobiotic piglet model of enterohemorrhagic *Escherichia coli* infection. Infect. Immun. 63:3621–3627.

23. McKee, M. L., A. R. Melton-Celsa, R. A. Moxley, D. H. Francis, and A. D. O'Brien. 1995. Enterohemorrhagic *Escherichia coli* O157:H7 requires intimin to colonize the gnotobiotic pig intestine and to adhere to HEp-2 cells. Infect. Immun. 63:3739–3744.

24. Sherman, P., F. Cockerill, R. Soni, and J. Brunton. 1991. Outer membranes are competitive inhibitors of *Escherichia coli* O157:H7 adherence to epithelial cells. Infect. Immun. 59:890–899.

25. Louie M., J. C. S. De Azavedo, M. Y. C. Handelsman, C. G. Clark, B. Ally, M. Dytoc, P. Sherman, and J. Brunton. 1993. Expression and characterization of the eaeA gene product of *Escherichia coli* serotype O157:H7. Infect. Immun. 61:4085–4092.

26. Toth, I., M. L. Cohen, H. S. Rumschlag, L. W. Riley, E. H. White, J. H. Carr, W. W. Bond, and I. K. Wachsmuth. 1990. Influence of the 60-Megadalton plasmid on adherence of *Escherichia coli* O157:H7 and genetic derivatives. Infect. Immun. 58:1223–1231.

27. Karch, H., J. Heesemann, R. Laufs, A. D. O'Brien, C. 0. Tacket, and M. M. Levine. 1987. A plasmid of Enterohemorrhagic *Escherichia coli* O157:H7 is required for expression of a new fimbrial antigen and for adhesion to epithelial cells. Infect. Immun. 55:455–461.

28. Ashkenazi, S., M. Larocco, B. E. Murray, and T. G. Cleary. 1992. The adherence of verocytotoxin-producing *Escherichia coli* to rabbit intestinal cells. J. Med. Microbiol. 37:304–309.

29. Fratamico, P. M., S. Bhaduri, and R. L. Buchanan. 1993. Studies on *Escherichia coli* serotype O157:H7 strains containing a 60-MDa plasmid and on 60-MDa plasmid-cured derivatives. J. Med. Microbiol. 39:371–381.

30. Junkins, A. D. and M. P. Doyle. 1989. Comparison of adherence properties of *Escherichia coli* O157:H7 and a 60-megadalton plasmid-cured derivative. Curr. Microbiol. 19:21–27.

31. Bilge, S. S., J. C. Vary,jr., S. F. Dowell, and P. I. Tarr. 1996. Role of the *Escherichia coli* O157:H7 0 side chain in adherence and analysis of an rfb locus. Infect. Immun. 64:4795–4801.

32. Barrett, T. J., M. E. Potter, and I. K. Wachsmuth. 1989. Bacterial endotoxin both enhances and inhibits the toxicity of Shiga-like toxin II in rabbits and mice. Infect. Immun. 57:3434–3437.

33. Yuhas, Y., A. Weizman, G. Dinari, and S. Ashkenazi. 1995. An animal model for the study of neurotoxicity of bacterial products and application of the model to demonstrate that Shiga toxin and lipopolysaccharide cooperate in inducing neurologic disorders. J. Infect. Dis. 171:1244–1249.

34. Oelschlaeger, T. A., T. J. Barrett, and D. J. Kopecko. 1994. Some structures and processes of human epithelial cells involved in uptake of enterohemorrhagic *Escherichia coli* O157:H7 strains. Infect. Immun. 62:5142–5150.

35. McKee, M. L. and A. D. O'Brien. 1995. Investigation of enterohemorrhagic *Escherichia coli* O157: H7 adherence characteristics and invasion potential reveals a new attachment pattern shared by intestinal *E. coli*. Infect. Immun. 63:2070–2074.

36. Tarr, P. 1. and M. A. Neill. 1996. Perspective: The problem of non-O157:H7 Shiga toxin (verocytotoxin)—producing *Escherichia coli*. J. Infect. Dis. 174:1136–1139.

37. Barrett, T. J., J. B. Kaper, A. E. Jerse, and I. K. Wachsmuth. 1992. Virulence factors in Shiga-like toxin-producing *Escherichia coli* isolated from humans and cattle. J. Infect. Dis. 165:979–980.

38. Chart, H., H. R. Smith, S. M. Scotland, B. Rowe, D. V. Milford, and C. M. Taylor. 1991. Serological identification of *Escherichia coli* O157:H7 infection in haemolytic uraemic syndrome. Lancet 337:138–140.

39. Barrett, T. J., J. H. Green, P. M. Griffin, A. T. Pavia, S. M. Ostroff, and I. K. Wachsmuth. 19. Enzyme-linked immunosorbent assays for detecting antibodies to Shiga-like toxin I, Shiga-like toxin II, and *Escherichia coli* O157:H7 lipopolysaccharide in human serum. Curr. Microbiol. 23:189–195.

40. Chart, H., S. M. Scotland, and B. Rowe. 1989. Serum antibodies to *Escherichia coli* serotype O157:H7 in patients with hemolytic uremic syndrome. J. Clin. Microbiol. 27:285–290.

41. Karmali, M. A., M. Petric, M. Winkler, M. Bielaszewska, J. Brunton, N. van de Kar, T. Morooka, G. B. Nair, S. E. Richardson, and G. S. Arbus. 1994. Enzyme-linked immunosorbent assay for detection of immunoglobulin G antibodies to *Escherichia coli* vero cytotoxin. J. Clin. Microbiol. 32:1457–1463.

42. Chart, H., D. Law, B. Rowe, and D. W. K. Acheson. 1993. Patients with haemolytic uraemic syndrome caused by *Escherichia coli* O157: Absence of antibodies to Vero cytotoxin 1 (VT1) or VT2. J. Clin. Pathol. 46:1053–1054.

43. Siddons, C. A. and P. A. Chapman. 1993. Detection of serum and faecal antibodies in haemorrhagic colitis caused by *Escherichia coli* O157. J. Med. Microbiol. 39:408–415.

44. Keusch, G. T., M. Jacewicz, M. M. Levine, R. B. Hornick, and S. Kochwa. 1976. Pathogenesis of Shigella diarrhea. Serum anticytotoxin antibodyresponse produced by toxigenic and nontoxigenic *Shigella dysenteriae* 1. J. Clin. Invest. 57:194–202.

45. Cohen, A., V. Madrid Marina, Z. Estrov, M. H. Freedman, C. A. Lingwood, and H. M. Dosch. 1990. Expression of glycolipid receptors to Shiga-like toxin on human B lymphocytes: a mechanism for the failure of long-lived antibody response to dysenteric disease. Int. Immunol. 2:1–8.

46. Scotland, S. M., B. Said, A. Thomas, and B. Rowe. 1994. Ability of human sera to neutralise the activity of Vero cytotoxins VT1, VT2 and variant forms of VT2. FEMS Microbiol. Lett. 115:285–290.

47. Yamada, S., A. Kai, and Y. Kudoh. 1994. Serodiagnosis by passive hemagglutination test and verotyoxin enzyme-linked immonosorbent assay of toxin-producing *Escherichia coli* infections in patients with hemolytic-uremic syndrome. J. Clin. Microbiol 32:955–959.

48. Jerse, A. E., J. Yu, B. D. Tall, and J. B. Kaper. 1990. A genetic locus of enteropathogenic *Escherichia coli* necessary for the production of attaching and effacing lesions on tissue culture cells. Proc. Natl. Acad. Sci. USA 87:7839–7843.

49. Jerse, A. E. and J. B. Kaper. 1991. The eae gene of enteropathogenic *Escherichia coli* encodes a 94-kilodalton membrane protein, the expression of which is influenced by the EAF plasmid. Infect. Immun. 59:4302–4309.

50. Kenny, B., L. Lai, B. B. Finlay, and M. S. Donnenberg. 1996. EspA, a protein secreted by enteropathogenic *Escherichia coli*, is required to induce signals in epithelial cells. Mol. Micro. 20:313–324.

51. Donnenberg, M. S., J. Yu, and J. B. Kaper. 1993. A second chromosomal gene necessary for intimate attachment of enteropathogenic *Escherichia coli* to epithelial cells. J. Bacteriol. 175:4670–4680.

52. Foubister, V., I. Rosenshine, M. S. Donnenberg, and B. B. Finlay. 1994. The eaeB gene of enteropathogenic *Escherichia coli* (EPEC) is necessary for signal transduction in epithelial cells. Infect. Immun. 62:3038–3040.
53. Jarvis, K. G., J. A. Girón, A. E. Jerse, T. K. McDaniel, M. S. Donnenberg, and J. B. Kaper. 1995. Enteropathogenic *Escherichia coli* contains a specialized secretion system necessary for the export of proteins involved in attaching and effacing lesion formation. Proc. Natl. Acad. Sci. USA 92:7996–8000.
54. Kenny, B. and B. B. Finlay. 1995. Protein secretion by enteropathogenic *Escherichia coli* is essential for transducing signals to epithelial cells. Proc. Natl. Acad. Sci. USA 92:7991–7995.
55. Johnson, R. P., W. C. Cray,jr., and S. T. Johnson. 1996. Serum antibody responses of cattle following experimental infection with *Escherichia coli* O157:H7. Infect. Immun. 64:1879–1883.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

We claim:

1. A method for diagnosing active infection of enterohemmorhagie *E. coli* (EHEC) comprising the steps of:
    (1) obtaining a body fluid or tissue sample from a subject who is suspected of being infected with EHEC while said subject is exhibiting symptoms of EHEC infection, said symptoms selected from the group consisting of diarrhea, bloody diarrhea or hemolytic uremic syndrome;
    (2) contacting said body fluid or tissue sample with an *E. coli* secreted protein (Esp) selected from the group consisting essentially of EspA or EspB;
    (3) using said Esp protein to detect the presence of antibodies which, are specific to said Esp protein in said body fluid or tissue sample, said antibodies recognizing said Esp protein and binding thereto; and
    (4) examining said Esp protein for the presence of said bound antibody, wherein the presence of said bound antibody indicates active infection with EHEC.

2. The method of claim 1, wherein the Esp protein is 37 kilodaltons.

3. The method of claim 1, wherein the Esp protein is 24 kilodaltons.

4. The method of claim 1, wherein the EHEC is *E. coli* O157:H7.

5. The method of claim 1, wherein the EHEC is Non-O157:H7 Shiga toxin-producing *E. coli* (STEC).

6. The method as claimed in claim 1, wherein said body fluid is selected from the group consisting of plasma, cerebrospinal fluid, saliva, semen, sweat, urine, and amniotic fluid.

7. The method as claimed in claim 6, wherein said body fluid is plasma.

8. The method as claimed in claim 1, wherein said tissue sample comprises lymphocytes.

9. The method of claim 1, wherein said detecting step is performed using a Western immunoblot.

10. The method of claim 1, wherein said detecting step is performed using an ELISA test.

11. The method of claim 1, wherein said subject is a human.

12. The method of claim 1, wherein said subject is a cow.

* * * * *

SEQUENCE LISTING

```
<160> NUMBER OF SEQ ID NOS: 2

<210> SEQ ID NO 1
<211> LENGTH: 937
<212> TYPE: DNA
<213> ORGANISM: Escherichia coli

<400> SEQUENCE: 1
atgaatacta ttgataatac tcaagtaacg atggttaatt ccgcttcgga gagtacgacc      60
ggcgcttcca gtgcagttgc cgcatctgct ttatcaattg attcatctct gcttactgat     120
ggtaaggttg atatttgtaa gctgatgctg gaaattcaaa aactcctcgg caagatggtg     180
actctattgc aggattacca acaaaaacaa ttggcgcaaa gctatcagat tcagcaggcc     240
gtttttgaga gccagaataa agctattgag gaaaaaaaag ccgcggcaac cgctgctttg     300
gttggcggga ttatttcatc agcattgggg atcttaggtt cttttgcagc aatgaacaac     360
gcggctaaag gggctggtga gattgctgaa aaagcaagct ctgcatcttc aaaggctgct     420
ggtgcggctt ctgaggttgc aaataaagct ctggtcaagg ctacggaaag tgttgctgat     480
gtcgcagagg aggcatccag tgcgatgcag aaagcgatgg ccacaacaac gaaagcagcc     540
agccgtgcat ctggcgttgc agatgatgtt gcgaaagcct ctgactttgc tgaaaatctt     600 gcagacccg ccgagaagac aagcagaatc aataagttgt tgaattccgt agataaactg      660
accaatacca cagcatttgt tgccgtgacc agtcttgctg aaggtacgaa aacgttgcca     720
acaacaatat ctgagtccgt caaatcgact catgaggtta atgaacaacg tgcgaagtcg     780
ctggaaaact tccagcaggg gaatctggag ctgtataaac aagacgttcg cagaacgcag     840
gatgatatca cgactcgtct gcgtgatata acgtccgctg tccgcgatct ccttgaggtc     900
cagaatcgta tggggcaatc gggtcgctta gctgggt                              937

<210> SEQ ID NO 2
<211> LENGTH: 312
<212> TYPE: PRT
<213> ORGANISM: Escherichia coli

<400> SEQUENCE: 2

Met Asn Thr Ile Asp Asn Thr Gln Val Thr Met Val Asn Ser Ala Ser
 1               5                  10                  15

Glu Ser Thr Thr Gly Ala Ser Ser Val Ala Ala Ser Ala Leu Ser
                20                  25                  30

Ile Asp Ser Ser Leu Leu Thr Asp Gly Lys Val Asp Ile Cys Lys Leu
            35                  40                  45

Met Leu Glu Ile Gln Lys Leu Leu Gly Lys Met Val Thr Leu Leu Gln
        50                  55                  60
```

```
Asp Tyr Gln Gln Lys Gln Leu Ala Gln Ser Tyr Gln Ile Gln Gln Ala
 65              70                  75                  80

Val Phe Glu Ser Gln Asn Lys Ala Ile Glu Glu Lys Lys Ala Ala Ala
                 85                  90                  95

Thr Ala Ala Leu Val Gly Gly Ile Ile Ser Ser Ala Leu Gly Ile Leu
                100                 105                 110

Gly Ser Phe Ala Ala Met Asn Asn Ala Ala Lys Gly Ala Gly Glu Ile
            115                 120                 125

Ala Glu Lys Ala Ser Ser Ala Ser Ser Lys Ala Ala Gly Ala Ala Ser
            130                 135                 140

Glu Val Ala Asn Lys Ala Leu Val Lys Ala Thr Glu Ser Val Ala Asp
145                 150                 155                 160

Val Ala Glu Glu Ala Ser Ser Ala Met Gln Lys Ala Met Ala Thr Thr
                165                 170                 175

Thr Lys Ala Ala Ser Arg Ala Ser Gly Val Ala Asp Asp Val Ala Lys
                180                 185                 190

Ala Ser Asp Phe Ala Glu Asp Leu Ala Asp Ala Ala Glu Lys Thr Ser
            195                 200                 205

Arg Ile Asn Lys Leu Leu Asn Ser Val Asp Glu Leu Thr Asn Thr Thr
210                 215                 220

Ala Phe Val Ala Val Thr Ser Leu Ala Glu Gly Thr Lys Thr Leu Pro
225                 230                 235                 240

Thr Thr Ile Ser Glu Ser Val Lys Ser Thr His Glu Val Asn Glu Gln
                245                 250                 255

Arg Ala Lys Ser Leu Glu Asn Phe Gln Gln Gly Asn Leu Glu Leu Tyr
                260                 265                 270

Lys Gln Asp Val Arg Arg Thr Gln Asp Asp Ile Thr Thr Arg Leu Arg
            275                 280                 285

Asp Ile Thr Ser Ala Val Arg Asp Leu Leu Glu Val Gln Asn Arg Met
        290                 295                 300

Gly Gln Ser Gly Arg Leu Ala Gly
305                 310
```